United States Patent [19]

Voorhees

[11] 4,088,756

[45] May 9, 1978

[54] PHARMACEUTICAL COMPOSITION AND PROCESS OF TREATMENT

[75] Inventor: John J. Voorhees, Ann Arbor, Mich.

[73] Assignee: The Regents of the University of Michigan, Ann Arbor, Mich.

[21] Appl. No.: 636,037

[22] Filed: Nov. 28, 1975

Related U.S. Application Data

[63] Continuation-in-part of Ser. No. 324,012, Jan. 16, 1973, abandoned, which is a continuation-in-part of Ser. No. 425,338, Dec. 17, 1973, abandoned.

[51] Int. Cl.² ............................................. A61K 31/70
[52] U.S. Cl. .................................................... 424/180
[58] Field of Search ........................................ 424/180

[56] References Cited

U.S. PATENT DOCUMENTS

| | | | |
|---|---|---|---|
| 3,819,830 | 6/1974 | Yoshimura et al. | 424/180 |
| 3,849,553 | 11/1974 | Dea et al. | 424/180 |
| 3,948,886 | 4/1976 | Shuman et al. | 424/180 |

*Primary Examiner*—Sam Rosen
*Attorney, Agent, or Firm*—Neal A. Waldrop

[57] ABSTRACT

A process and pharmaceutical compositions for alleviating proliferative skin diseases such as psoriasis, atopic dermatitis, etc., comprising administering to humans, or domesticated animals, topically, and/or parenterally, and/or systemically a composition comprising a pharmaceutical carrier and at least one active compound selected from the groups, $\alpha$, $\beta_1$, and $\beta_2$ adrenergic agents, and oral hypoglycemic agents.

2 Claims, No Drawings

4,088,756

PHARMACEUTICAL COMPOSITION AND PROCESS OF TREATMENT

CROSS-REFERENCE TO RELATED APPLICATIONS

This application is a continuation-in-part of prior copending application Ser. No. 425,338, filed Dec. 17, 1973, which is a continuation-in-part application of prior copending application Ser. No. 324,012, filed Jan. 16, 1973, for "Pharmaceutical Composition and Process of Treatment", both of which became abandoned after the filing date of the above identified successor application.

BRIEF DESCRIPTION OF THE INVENTION

This invention relates to pharmaceutical compositions for and a method of treating psoriasis and related skin diseases characterized by epidermal cell proliferation. The compositions may be applied topically or by injection such that the composition enters the blood stream, or intralesionally, or intradermally, or subcutaneously or orally. The treatment may be either therapeutic or prophylactic.

DETAILED DESCRIPTION OF THE INVENTION

Humans and domesticated animals are afflicted with a wide variety of skin disorders or diseases. This invention relates to the treatment of that portion of skin diseases which is characterized by epidermal cell proliferation, or division, and may also be associated with incomplete tissue differentiation. Such diseases do not include carcinomas of the skin nor changes in skin cells during aging, or during the normal skin replacement cycle. Psoriasis is the most serious of the skin diseases with which this invention is concerned. These skin diseases are designated, in this specification and in the claims as "proliferative skin diseases" and other examples include atopic dermatitis, non-specific dermatitis, primary irritant contact dermatitis, allergic contact dermatitis, lamellar ichthyosis, epidermolytic hyperkeratosis, premalignant sun-induced keratosis, non-malignant keratosis and seborrheic dermatitis in humans, and atopic dermatitis and mange in domesticated animals.

Heretofore, proliferative skin diseases have been generally accepted by mankind as an ongoing evil having degrees of severity variable with time, with inherited skin traits and external factors but always have been recognized as unsightly, painful, morbid diseases. Over the history of mankind innumerable medicines and treatments have been proposed, tried and used with varying degrees of success. However, no treatment heretofore devised or pharmaceutical composition used has been entirely successful.

The present day treatments of a commercial nature which are prescribed and used for the treatment of proliferative skin diseases include three approaches: (1) topical applications: coal tar derivatives, 5 fluorouracil, vitamin A acid, glucocorticoids in high dosage (constituting a non-permissive concentration), bath oils and non-specific emollient creams and ointments; (2) the systemic administration: glucocorticoids and classic anti-cancer agents, for example, methothrexate, hydroxyurea, azaribine, cyclophosphamide; (3) physical modalities; ultra violet light, x-irradiation, and in severe cases, surgery.

While these treatments provide, in certain cases, some remission of the original symptoms, each treatment suffers some defect, for example, temporary and/or incomplete mitigation of symptoms, rapid re-occurrence of the disease when treatment is terminated, serious and sometimes irreversible damage (atrophy) resulting from the topical application for extended times of glucocorticoids, acute bone marrow suppression and cirrhosis of the liver resulting from the protracted use of methothrexate which may lead to death of the patient, and the causation of cancer by the application of anticancer drugs, x-irradiation, or ultra violet rays.

Psoriasis is well-known to afflict two to three percent of the earth's population and is considered by most to be one of man's most unsightly, painful, morbid diseases. Psoriasis is a complex disorder of many varieties and is not completely medically understood even though extensive research and effort has been expended in the attempt to determine and identify its cause and to provide a cure. It is known that the epidermis of a psoriasis patient is characterized by excessive cell proliferation, incomplete terminal differentiation and glycogen accumulation. Although many compositions and methods for alleviating psoriasis have been proposed and used, only certain of them have been successful; even those considered successful usually alleviated the disease only for temporary periods. There is still a need for improved compositions and methods for treating psoriasis.

Previously existent compositions and treatments for psoriasis have provided in certain cases some remission of the original symptoms, or a temporary cure, but each composition or treatment heretofore known suffers from some defect to some degree. For a treatment to constitute a cure for psoriasis, it must be both safe and effective to cause an enduring remission of all the psoriasis lesions on the body to a degree such that they disappear and the skin assumes a normal appearance and is healthy and functional on a continuing basis. Alleviation of psoriasis to a degree less than a complete cure is useful and desirable because a treatment which accomplishes an alleviation in a seriously afflicted patient may be satisfactory to effect a substantially complete or permanent cure in a less seriously afflicted patient.

The primary object of this invention is to provide a pharmaceutical composition suitable for and a method of treating proliferating skin diseases. One of the more specific primary objectives of this invention is to provide a pharmaceutical composition for administration to psoriasis patients which is both capable of alleviating psoriasis and safe in application, even over an extended time period. Another object of this invention is to provide a method for treatment of psoriasis which is capable of effecting alleviation of the psoriasis in a short time period. A further object is to provide a cure for psoriasis, i.e., one which prevents a re-occurrence of the disease when the treatment is terminated.

In accordance with this invention it has been found that proliferative skin diseases are alleviated, that is, the symptoms of the disease are noticeably improved or become undetectable, by the treatment of the afflicted patient, or animal, with one or more of the pharmaceutical compositions described in detail hereinbelow.

For the purposes of this specification and the claims, a proliferative skin disease is alleviated when there is a noticeable decrease in the thickness of a lesion to palpation, with or without residual redness, or residual slightly dilated blood vessels or residual hyper- or hypo-pigmentation. For purposes of this invention and as claimed herein, psoriasis is alleviated when a scale-free psoriasis lesion is noticeably decreased in thickness, or noticeably but incompletely cleared, or completely cleared; indications of such alleviation include restoration of cell proliferation rate, and/or terminal differentiation, and/or glycogen content to near normal levels.

The compositions of this invention may be applied topically or by injection such that the composition enters the blood stream, or intradermally, intro- or peri-lesionally, or sub-cutaneously.

The term "topical" as employed herein relates to the use of the active ingredient incorporated in a suitable pharmaceutical carrier, and applied at the site of the disease for exertion of local action. Accordingly, such topical compositions include those pharmaceutical forms in which the compound is applied externally by direct contact with the skin surface to be treated. Conventional pharmaceutical forms for this purpose include ointments, lotions, pastes, jellies, sprays, aerosols, bath oils and the like. The term "ointment" embraces formulations (including creams) having oleaginous, absorption, water-soluble and emulsion-type bases, e.g., petrolatum, lanolin, polyethylene glycols, as well as mixtures thereof. It has been found that topical application with occlusion of an area larger than the medicated area produces improved results relative to non-occluded topical application and is, therefore, the preferred method of topical treatment with the compositions of this invention.

Certain of the compositions of this invention advantageously include skin penetrating adjuvants such as, for example, dimethyl sulfoxide, dimethyl acetamide, etc.

Injection "intradermally" refers to positioning the composition in the high dermis by needle injection, or by high pressure air injection.

Injection "intra- or peri-lesionally" refers to positioning the composition into the lesion or into the tissue adjacent to the lesion.

The compositions may be injected so as to reach the blood stream intramuscularly, subcutaneously, rectally by suppositories, sublingually, intravenously, orally, by inhalation, or by application to non-diseased skin.

The best mode of practicing the process of this invention is to treat the afflicted animal, or human, so as to cause a continuing release of the active compound at the afflicted site or sites, at a selected, controlled rate which is sustained for an extended time period. For example, epinephrine will be continuously released and provides sustained epinephrine activity for 9–10 hours by employing an aqueous suspension of crystalline epinephrine 1:200, in a sterile solution containing 0.5% phenol, 0.5% sodium thioglycollate, 1% sodium ascorbate, and 25% glycerine in water. This suspension may be administered subcutaneously in a dosage of 0.1–0.3 cc. of the suspension. Epinephrine activity is obtained substantially immediately from the epinephrine in suspension. Various modifications of the suspension ingredients, compatible with the particular active compound selected for injection may be made to obtain the desirable continuing and sustained active compound activity at the site being treated. Moreover, appropriate substitutions for the above mentioned suspension ingredients may be made to accommodate the selected active compound for topical or systemic administration to the afflicted patient, and similar enhanced results are obtained from such applications when the active compound is released over an extended time period.

The compositions of this invention comprise a pharmaceutical carrier and about 0.1% to about 15%, weight/volume, of at least one of the compounds selected from the groups:

I A compound of the formula

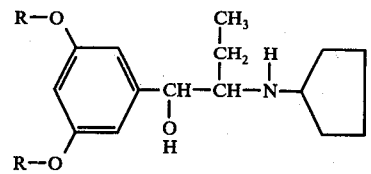

wherein R is hydrogen or acyl of an aliphatic carboxylic acid of from 2 to 5 carbon atoms, inclusive, including the pharmacologically acceptable acid addition salts thereof;

II A compound of the formula

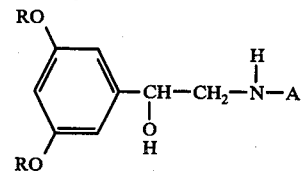

wherein R is hydrogen or acyl of an aliphatic carboxylic acid of from 2 to 5 carbon atoms inclusive including the pharmacologically acceptable acid addition salts thereof

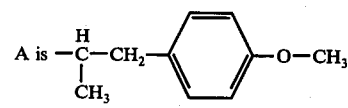

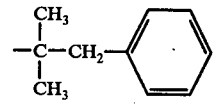

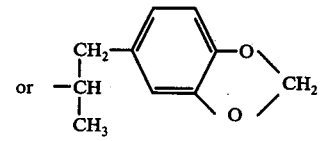

including the pharmacologically acceptable acid addition salts thereof;

III A compound of the formula

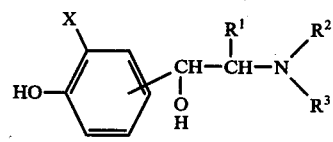

wherein $R^1$ is hydrogen or alkyl of from 1 to 6 carbon atoms inclusive, $R^2$ is hydrogen or benzyl, $R^3$ is hydrogen, alkyl of from 1 to 6 carbon atoms inclusive or hydroxy or amino substituted forms thereof; a heterocyclic residue; cycloalkyl, aralkyl or aryloxyalkyl or hydroxy or alkoxy substituted forms thereof; and X is hydroxyalkyl of from 1 to 6 carbon atoms inclusive, hydroxy substituted aralkyl, -CO$_2$-alkyl, hydroxyaminocarbonyl, hydrazinocarbonyl or amide of the formula —CONR⁵R⁸ where $R^5$ and $R^6$ are hydrogen, alkyl of from 1 to 6 carbon atoms inclusive and optionally substituted by hydroxy or amino or $NR^5R^6$ from a heterocyclic ring including the pharmacologically acceptable acid addition salts thereof;

IV A compound of the formula

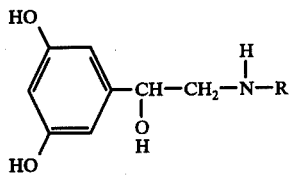

wherein R is isopropyl, tert-butyl,

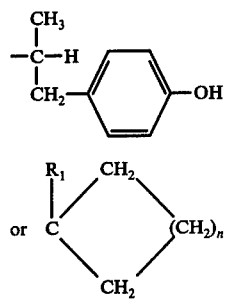

or

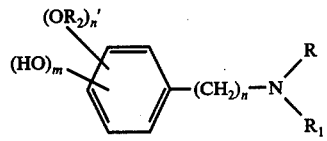

wherein $n$ is 0 to 3, inclusive, $R_1$ is hydrogen, methyl or ethyl including the parmacologically acceptable acid addition salts thereof;

V A compound of the formula

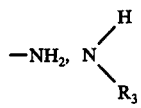

wherein $m$ is from 0 to 2, $n$ is 1–8 including both straight and branched chains and can be optionally substituted with hydroxy or carboxy. R is hydrogen, alkyl of 1 to 3 carbon atoms, cycloalkyl of 3 to 7 carbon atoms, or aralkyl in which alkyl is of 1 to 6 carbon atoms; $R_1$ is hydrogen, alkyl of 1 to 3 carbon atoms, cycloalkyl of 3 to 7 carbon atoms, aralkyl in which alkyl is 1 to 6 carbon atoms,

—NH₂, N⟨H/R₃ wherein $R_3$ is an amide bonded amine acid, $R_2$ is H or methyl, $p$ is 0 or 1;

VI Adenosine and its analogs, including: 2'-deoxyadenosine; 2',3'-isopropylidene adenosine; toyocamycin; 1-methyladenosine; N-6-methyladenosine; adenosine N-oxide; 6-methylmercaptopurine riboside; 6-chloropurine riboside, 5'-adenosine monophosphate; and VII A member selected from the group consisting of amantadine, tolbutamide, chlorpropamide, tolazamide, acetohexamide and phenformin, said compounds being in association with a pharmaceutical carrier wherein the concentration of said active component is about 0.1% to about 1.5% by weight of said composition.

The compositions of this invention may be employed in conjunction with glucocorticoids. The expression "glucocorticoids" refers to a naturally occurring product of the adrenal cortex, or a synthetic analog thereof possessing anti-inflammatory activity and minimal or no mineralocorticoid activity or sex steroid activity. Of the natural glucocorticoids, one may use for example, hydrocortisone or the synthetic glucocorticoids such as methyl prednisolone acetate (Prednisone) for oral application or triamcinolone for topical therapy. The glucocortcoids should be employed in minor amounts or "permissive dosage." The expression "permissive dosage" for glucocorticoids refers to a quantity which minimally supplements the natural output of adrenal cortical glucocorticoids in a normal person and which dosage administered, alone, has no perceptible effect on proliferative skin diseases.

The quantity of the active compound to be used in the compositions of this invention for administration topically, parenterally or systemically ranges from about 0.1% to about 15% weight/volume topically; from about 0.1% to about 10% w/v parenterally; and for oral dosage forms the % amount of active ingredient is determined by the physical characteristics of the carrier with regard to manufacturing requirements and elegance.

The compositions of the present invention are presented for systemic administration to humans and animals in unit dosage forms, such as tablets, capsules, pills, powders, granules, sterile parenteral solutions or suspensions, and oral solutions or suspensions, and oil-water emulsions containing suitable quantities of one or more of the active compounds above described.

For oral administration either solid or fluid unit dosage forms can be prepared. For preparing solid compositions such as tablets, the principal active ingredient is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. The tablets can be laminated or otherwise compounded to provide a dosage form affording the advantage of prolonged or delayed action or predetermined successive action of the enclosed medication. For example, the tablet can comprise an inner dosage and an outer dosage component, the latter being in the form of an envelope over the former.

Alternatively, the two component system can be utilized for preparing tablets containing two or more incompatible active ingredients. Wafers are prepared in the same manner as tablets, differing only in shape and the inclusion of sucrose or other sweetener and flavor. In their simplest embodiment, capsules, like tablets, are prepared by mixing the active compound or compounds with an inert pharmaceutical diluent and filling the mixture into a hard gelatin capsule or appropriate size. In another embodiment, capsules are prepared by filling hard gelatin capsules with polymeric acid coated beads containing the active compound or compounds. Soft gelatin capsules are prepared by machine encapsulation of a slurry of the active compound or compounds with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydro-alcoholic (ethanol) vehicle with suitable sweeteners such as sugar and saccharin, together with an aromatic flavoring agent.

Suspensions can be prepared of the insoluble forms with a syrup vehicle with the aid of a suspending agent such as acacia, tragacanth, methylcellulose and the like.

Topical ointments can be prepared by dispersing the active compound or compounds in a suitable ointment base such as petrolatum, lanolin, polyethylene glycol, mixtures thereof, and the like. Advantageously, the active compound or compounds is finely divided by means of a colloid mill utilizing light liquid petrolatum as a levigating agent prior to dispersing in the ointment base. Topical creams and lotions are prepared by dispersing the active compound or compounds in the oil phase prior to the emulsification of the oil phase in water.

For parenteral administration the dosage forms are prepared utilizing the active compound or compounds and a sterile vehicle, water being preferred. The compound, depending on the form and concentration used, can be either suspended or dissolved in the vehicle. In preparing solutions, a water-soluble form of the compound can be dissolved in water for injection and filter sterilized before filling into a suitable vial or ampul and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution.

For parenteral or systemic administration of the compositions of this invention, the usual dosage of the selected active compound, or compounds, should be employed.

The compositions of this invention may include one or more of the above identified active compounds in a single composition or the method of the invention may be practiced by the administration of a plurality of compositions, each of which contains a single or a plurality of active compounds. In certain cases, the method of the invention may involve the administration of compositions containing a single active compound or a mixture of active compounds by a plurality of the forms of the administration, for example by a combination of oral and/or injection and/or topical application, etc.

In other cases the method of this invention is advantageously practiced by combining the administration forms in a time spaced sequence, for example, by using systemic application of one or more of the compositions for a time period and then applying one or more compositions topically, or by injection while continuing the systemic application, etc.

The following examples identify certain compositions which typify the manner of combining selected active compounds with a pharmaceutical carrier for use in the process of treatment of proliferative skin diseases as above generally described, but they are not intended to represent the limits of either the compositions of or the process of this invention which is defined in the claims.

EXAMPLE 1 Capsules

One thousand two-piece hard gelatin capsules for oral use, each containing 200 mg. of adenosine are prepared from the following types and amounts of materials:

| | |
|---|---|
| Adenosine | 200 gm. |
| Corn starch | 150 gm. |
| Talc | 75 gm. |
| Magnesium stearate | 2.5 gm. |

The materials are thoroughly mixed and then encapsulated in the usual manner.

The foregoing capsules are useful for the systemic treatment of psoriasis in adult humans by the oral administration of 1 capsule every 4 hours.

Using the procedure above, capsules are similarly prepared containing in 5, 50, and 100 mg. amounts by substituting 5, 50, and 100 gm. of adenosine for the 200 gm. used above.

EXAMPLE 2 Capsules

One thousand two-piece hard gelatin capsules for oral use, each containing 500 mg. of adenosine are prepared from the following types and amounts of ingredients:

| | |
|---|---|
| Adenosine | 500 gm. |
| Corn starch | 250 gm. |
| Talc | 75 gm. |
| Magnesium stearate | 2.5 gm. |

The ingredients are thoroughly mixed and then encapsulated in the usual manner.

The foregoing capsules are useful for the systemic treatment of psoriasis in adult humans by the oral administration of 1 capsule twice a day.

EXAMPLE 3 Tablets

One thousand tablets for oral use, each containing 50 mg. of adenosine are prepared from the following types and amounts of materials:

| | |
|---|---|
| Adenosine | 50 gm. |
| Lactose | 125 gm. |
| Corn starch | 65 gm. |
| Magnesium stearate | 7.5 gm. |
| Light liquid petrolatum | 3 gm. |

The ingredients are thoroughly mixed and slugged. The slugs are broken down by forcing through a number sixteen screen. The resulting granules are then compressed into tablets, each tablet containing 50 mg. of adenosine.

The foregoing tablets are useful for systemic treatment of psoriasis in adult humans by oral administration of 1 tablet every 4 hours.

EXAMPLE 4 Oral syrup

One thousand cc. of an aqueous suspension for oral use, containing in each 5 cc. dose 200 mg. of adenosine is prepared from the following types and amounts of ingredients:

| | |
|---|---|
| Adenosine | 40 gm. |
| Citric acid | 2 gm. |
| Benzoic acid | 1 gm |
| Sucrose | 700 gm. |
| Tragacanth | 5 gm. |
| Lemon oil | 2 cc. |
| Deionized water q.s. | 1000 cc. |

The citric acid, benzoic acid, sucrose, tragacanth, and lemon oil are dispersed in sufficient water to make 850 cc. of solution. The adenosine is stirred into the syrup until uniformly distributed. Sufficient water is added to make 1000 cc.

The composition so prepared is useful in the systemic treatment of psoriasis in adult humans at a dose of 1 teaspoonful 4 times a day.

EXAMPLE 5 Parenteral solution

A sterile aqueous solution for intramuscular use, containing in 1 cc. 50 mg. of adenosine is prepared from the following types and amounts of materials:

| | |
|---|---|
| Adenosine | 50 gm. |
| Lidocaine hydrochloride | 4 gm. |
| Methylparaben | 2.5 gm. |
| Propylparaben | 0.17 gm. |
| Water for injection q.s. | 1000 cc. |

The ingredients are dissolved in the water and the solution sterilized by filtration. The sterile solution is filled into vials and the vials sealed.

The composition is useful in the systemic treatment of psoriais at a dose of 1 cc. I.M. 4 times a day.

EXAMPLE 6 Parenteral solution

A sterile aqueous solution for intradermal use, containing in 1 cc. 5 mg. of adenosine is prepared from the following types and amounts of ingredients:

| | |
|---|---|
| Adenosine | 5 gm. |
| Sodium chloride 10% solution q.s. | |
| Water for injection q.s. | 1000 cc. |

The adenosine is added to the water and sufficient sodium chloride added to form an isotonic solution and the solution sterilized by filtration.

The sterile solution is administered intradermally by high pressure injection for treatment of psoriasis.

EXAMPLE 7 Topical ointment

One thousand gm. of 0.25% ointment is prepared from the following types and amounts of ingredients:

| | |
|---|---|
| Adenosine | 2.5 gm. |
| Liquid petrolatum (heavy) | 250 gm. |
| Wool fat | 200 gm. |
| White petrolatum q.s. | 1000 gm. |

The white petrolatum and wool fat are melted and 100 gm. of liquid petrolatum added thereto. The adenosine is added to the remaining liquid petrolatum and the mixture milled until the powder is finely divided and uniformly dispersed. The powder mixture is stirred into the white petrolatum mixture and stirring continued until the ointment congeals.

The foregoing ointment is usefully applied topically to the skin of animals for the treatment of mange.

EXAMPLE 8 Cream

One thousand grams of a topical cream are prepared from the following types and amounts of ingredients:

| | |
|---|---|
| Adenosine | 50 gm. |
| Tegacid Regular* | 150 gm. |
| Spermaceti | 100 gm. |
| Propylene glycol | 50 gm. |
| Polysorbate 80 | 5 gm. |
| Methylparaben | 1 gm. |
| Deionized water q.s. | 1000 gm. |

*Self-emulsifying glyceryl monostearate from Goldschmidt Chemical Corporation, New York, N.Y.

Schmidt Chemical Corporation, New York, N.Y.

The Tegacid and spermaceti are melted together at a temperature of 70°–80° C. The methylparaben is dissolved in about 500 gm. of water and the propylene glycol, polysorbate 80, and adenosine are added in turn, maintaining a temperature of 75°–80° C. The methylparaben mixture is added slowly to the Tegacid and spermaceti melt, with constant stirring. The addition is continued for at least 30 minutes with continued stirring until the temperature has dropped to 40°–45° C. The pH of the final cream is adjusted to 3.5 by adding 2.5 gm. of citric acid and 0.2 gm. of dibasic sodium phosphate dissolved in about 50 gm. of water. Finally, sufficient water is added to bring the final weight to 1000 gm. and the preparation stirred to maintain homogeneity until cooled and congealed.

The foregoing composition is useful for the treatment of psoriasis by applying to the lesions with occlusive bandage.

EXAMPLE 9 Cream

| | |
|---|---|
| Adenosine | 1000 gm. |
| Cetyl alcohol | 600 gm. |
| Stearyl alcohol | 600 gm. |
| Aerosol OT | 150 gm. |
| White petrolatum | 3000 gm. |
| Propylene glycol | 1000 ml. |
| Distilled water q.s. | 10,000 gm. |

The adenosine is mixed with the white petrolatum and stirred with a melt of the alcohols and propylene glycol. The aerosol OT is dissolved in 5000 cc. of water and an emulsion formed with the petrolatum mix, sufficient water being added to make 10,000 grams.

The cream is applied to psoriatic lesions twice daily with occlusive bandage.

Optionally, following the procedure of the preceding example, substituting 2,000 grams of dimethylacetamide for 2,000 grams of water a composition is obtained providing better penetration of the active ingredient into the skin.

EXAMPLE 10

Following the procedure of the preceding Examples 1 to 9, inclusive, substituting a therapeutic dosage amount each of 1(3,5-dihydroxyphenyl)-2-cyclopentylaminobutanol, 1(3,5-dihydroxyphenyl)-2-[1-(p-methoxyphenyl)isopropylamino]ethanol, isoetharine, orciprenaline, methoxyphenamine, chlorpropamide, and tolbutamide for the adenosine, compositions are prepared which are useful for the treatment of psoriasis.

EXAMPLE 11

The compositions prepared in the preceding examples 1 through 10, inclusive, can similarly be administered for treatment of atopic dermatitis, non-specific dermatitis, primary irritant contact dermatitis, allergic contact dermatitis, lamellar ichthyosis, epidermolytic hyperkeratosis, premalignant sun induced keratosis, nonmalignant keratosis, and seborrheic dermatitis in humans and atopic dermatitis and mange in domesticated animals.

EXAMPLE 12

Advantageously following the therapy of Examples 1 to 10 additional benefits ca be obtained with concurrent or sequential oral administration of 20 mg. of prednisone twice a week.

EXAMPLE 13

A series of tests to determine the level of cyclic adenosine monophosphate concentration, cyclic AMP, as the result of incubation of hairless mouse epidermis with various compounds in beakers, was carried out in the following manner:

The hairless mouse epidermis was incubated in a beaker containing Kreb's-Ringer bicarbonate buffer solution, with added glucose, by agitation for 20 minutes in a water bath at 37° C; a series of beakers were prepared and at the end of the 20-minute agitation period the active compound was added, in the concentration set forth in the table below, and the hairless mouse epidermis sample was removed after incubation for 5 minutes, another sample after incubation for 10 minutes and a third sample after incubation for 15 minutes, each test being carried out at least three times. The removed samples were quick-frozen in liquid nitrogen and prepared for cyclic AMP concentration determination by grinding, homogenizing in trichloroacetic acid, purification by column chromatography, and then assayed for cyclic AMP using the protein binding method of Gilman.* The results are reported in percent increase in the cyclic AMP concentration from the concentration in the hairless mouse epidermis, incubated without the test compound at the same time points, as set forth in Table I
* Gilam AG: A protein binding assay for adenosine 3' : 5' - cyclic monophosphate Proc Natl Acad Sci USA 67:305-312, 1970.

TABLE I

| Compounds Incubated With Hairless Mouse Epidermal Slices | | % Increase in Cyclic AMP Concentrations - Incubation Times | | |
| --- | --- | --- | --- | --- |
| Compound | Concentration-Molar | 5 Min. | 10 Min. | 15 Min. |
| Adenosine | $5 \times 10^{-6}$ M | 0 | 0 | 0 |
| | $5 \times 10^{-5}$ M | 0 | 0 | 0 |
| | $5 \times 10^{-4}$ M | 169.9 | 61.9 | 25.4 |
| | $7 \times 10^{-4}$ M | 83.6 | 76.6 | 51.4 |
| | $3 \times 10^{-3}$ M | 128.5 | 351.5 | 226.7 |
| | $3.2 \times 10^{-3}$ M | 68 | 38 | 42 |
| | $5 \times 10^{-3}$ M | 209.9 | 230.6 | 227.8 |
| | $8 \times 10^{-3}$ M | 185 | 123 | 114 |
| | $1 \times 10^{-2}$ M | 250 | 327 | 186 |

TABLE I-continued

| Compounds Incubated With Hairless Mouse Epidermal Slices | | % Increase in Cyclic AMP Concentrations - Incubation Times | | |
| --- | --- | --- | --- | --- |
| Compound | Concentration-Molar | 5 Min. | 10 Min. | 15 Min. |
| 5'AMP | $5 \times 10^{-3}$ M | 210 | 310 | 386 |

Based upon these results, it is concluded that adenosine and 5'AMP are effective in causing an increase in cyclic AMP concentration in the epidermis of mammalian skin.

The variation in cyclic AMP concentration in tissue slices from psoriasis patients, in vitro, using ethyl adenosine-5'-caboxylate at a concentration of $1 \times 10^{-3}$ molar was measured in the following manner:

Psoriatic tissue slices were removed from a psoriasis patient from the psoriasis lesion, per se, designated "involved" and from other portions of the epidermis of the same patient, designated "uninvolved", as shown in Table II, below. The tissue slices were incubated for 15 minutes in 37° C in a beaker containing Kreb's -Ringer bicarbonate buffer solution with added glucose and agitation, and at the end of the preincubation period, the said ethyl adenosine-5' carboxylate was added in a concentration of $1 \times 10^{-3}$ M to beakers containing both the involved and uninvolved epidermis psoriatic tissue slices. A minimum of three samples, each, of said uninvolved and involved tissue slices were maintained in contact with said ethyl adenosine-5-carboxylate for 7 minutes or 10 minutes and withdrawn. The samples were prepared for cyclic AMP assay in the same manner as described above for the hairless mouse epidermis samples and the results of said tests are set forth below in Table II:

The results are set forth in pmoles of c-AMP per microgram of DNA, and also in terms of percent increase in the cyclic AMP concentration. The lower percent increases in the involved samples are due to an increase in the baseline values of the involved tissue.

The decrease in cyclic AMP levels in the involved tissue after 10 minutes of incubation shows that the maximum c-AMP elevation occurs after about 7 minutes.

TABLE II

| | PSORIATIC TISSUE SLICES | | | |
| --- | --- | --- | --- | --- |
| ETHYL ADENOSINE CARBOXYLATE | % Increase In c-AMP Concentration | | Picomoles of c AMP per Microgram of DN | |
| | UNINVOLVED | INVOLVED | UNINVOLVED | INVOLVED |
| $1 \times 10^{-3}$ M | | | | |
| 7 Min. Incubation | 117 | 77 | 1.52 | 1.72 |
| 10 Min. Incubation | 166 | 37 | 1.57 | 1.25 |

Based upon the tests described and the results thereof set forth in Table II, it is apparent that ethyl adenosine carboxylate causes an increase in c-AMP concentration in psoriatic tissue slices removed from humans where the tissue is involved or uninvolved from the same patient.

An improved form of this invention has now been found whereby posriasis may be alleviated in a shorter time and to a greater than expected degree than obtainable by the processes described hereinabove. This improved invention comprises the concurrent administration to an afflicted human or animal of a composition comprising active compounds in association with a pharmaceutical carrier wherein said compounds are present in an amount in the range of about 0.1% to about 10% w/v, the composition containing at least one active compound selected from each of two groups.

The first group of active compounds consists of adenosine, 2'-deoxyadenosine, 2', 3'-isopropylidene adenosine, toyocamycin, 1-methyladenosine, N-6-methyladenosine, adenosine N-oxide, 6-methylmercaptopurine riboside, 6-chloropurine riboside, 5'-adenosine monophosphate.

The second group of active compounds consists of papaverine, diazepam, 1-ethyl-4-(isopropylidenehydrazino)-1$_H$-pyrazolo-(3,4-b)-pyridine-5-caboxylic acid, ethyl ester, HCl, and a compound having the formula:

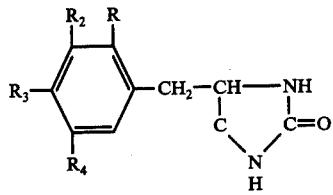

wherein R is halogen, hydrogen, lower alkyl and lower alkoxy; $R_2$, $R_3$ and $R_4$ taken independently of each other are hydrogen, lower alkoxy or hydroxy-lower alkoxy and provided that $R_2$, $R_3$ and $R_4$ taken independently of each other represent at least one oxygenated substituent; R, $R_2$, $R_3$ and $R_4$ taken as an adjacent pair is methylenedioxy and the optical antipodes thereof.

The combination of material from Group I and Group II is even further enhanced in its ability to alleviate psoriasis, as to time or concentration of the material from Group I or Group II which is required to be effective, by the inclusion in the combination of a glucocorticoid. The expression "glucocorticoid" refers to a naturally occurring product of the adrenal cortex, or a synthetic analog thereof possessing anti-inflammatory activity and minimal or no mineralocorticoid activity or sex steroid activity. Of the natural glucocorticoids, one may use for example, hydrocortisone or the synthetic glucocorticoids such as methyl prednisolone acetate (Prednisone) for oral application or triamcinolone for topical therapy.

The quantity of the compounds from Groups I or II to be used in the compositions of this invention for administration topically, parenterally or systemically ranges from about 0.1% to about 10% w/v topically; from about 0.1% to about 10% w/v parenterally or orally. The amount of each of the materials from Groups I and II or any particular composition may be varied over a wide range depending upon the severity of the psoriasis, the patient's reaction to drugs, as above generally described in connection with the over-all objective of safety of administration; the quantity of each of the materials from Group I and Group II also varies as a function of degree of synergism which results from a particular combination of materials that is selected with the over-all objective being the selection of the minimal quantity of each material of the combination which will provide alleviation of the psoriasis in the particular patient. For example, the degree of synergism exhibited by the combination of isoproterenol and theophylline exceeds the synergism resulting from the combination of adenosine and papaverine.

Thus, the quantity of isoproterenol and theophylline may satisfactorily range from one-hundredth of the amount of isoproterenol which is required to activate the epidermal adenolate cyclase to a degree sufficient to alleviate psoriasis up to an amount of about one-third the quantity of isoproterenol which is effective for that purpose, and the quantity of theophylline may satisfactorily vary from about one-hundredth of the amount of theophylline which is required to inhibit epidermal phosphodiesterase to a degree sufficient to alleviate psoriasis when applied separately, up to an amount of about one-third the quantity of theophylline sufficient to effectively alleviate psoriasis. In contrast, the range for adenosine in combination with papaverine may satisfactorily vary from about one-tenth the amount of adenosine which is required to alleviate psoriasis, when applied alone up to an amount of about one-third the quantity required to alleviate psoriasis when applied alone in combination with about one-tenth the amount of apapverine up to about one-third of the amount of papaverine required to effectively inhibit epidermal phosphodiasterase when applied alone, in order to achieve the synergistic cooperation to alleviate psoriasis when administered in combination. In general, the minimum quantity of the selected material from Group I may satisfactorily form about 1/100th to about 1/3rd of the amount of that material which is effective to alleviate psoriasis when applied alone and the amount of the material selected from Group II may satisfactorily vary from about 1/100th to about 1/3rd of the amount of that material which is effective to alleviate psoriasis when applied alone. When the combination also includes a permissive dose of a glucocorticoid, the quantities of the selected material from Group I and from Group II may each be decreased, or one of them may be decreased to as much as one-half of its previously selected effective concentration. From the standpoint of the greatest combination or safety and effectiveness it is preferred that the combination include a glucocorticoid. In the presence of a permissive dose of a glucocorticoid in the composition, the quantities of the material selected from Group I may vary from about 1/100th to about ⅓ of the amount of that selected compound which is effective to alleviate psoriasis when applied alone and the amount of the material selected from Group II may vary from about 1/100th to about 166 of the amount effective to alleviate psoriasis when applied alone. In most instances, it is preferred to slightly exceed the minimum quantity determined to be effective and to produce the desired synergistic result in any given composition, for example, it is desirable to employ 174 to ⅓ more of each of the compounds from Group I and Group II which is established as the minimum effective composition for a given patient since such composition has wider general utility and exhibits satisfactory safety characteristics for a wide range of psoriasis patients.

I claim:

1. A process for treating proliferative skin dieseases which comprises administering to the afflicted human or animal a composition comprising at least two active compounds in association with a pharmaceutical carrier, said compounds being present in an amount in the range of about 0.1% to about 10% w/v which is effective to alleviate a proliferative skin disease, at least one of said compounds being selected from a first group consisting of adenosine, 2'-deoxyadenosine, 2',3'-isopropylidene adenosine, toyocamycin, 1-methyladenosine, N-6-methyladenosine, adenosine N-oxide, 6-methylmercaptopurine riboside, 6-chloropurine riboside, 5'-adenosine monophosphate, and at least one of said compounds being selected from a second group consisting of papaverine, diazepam, 1-ethyl-4-(isopropylidenehydrazino)-1$_H$-pyrazolo-(3,4-b)-pyridine-5-carboxylic acid, ethyl ester, HCl, and a compound having the formula:

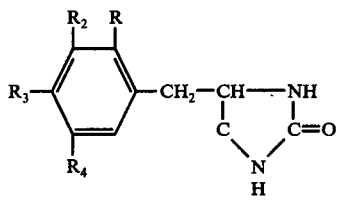

wherein R is halogen, hydrogen, lower alkyl and lower alkoxy; $R_2$, $R_3$ and $R_4$ taken independently of each other are hydrogen, lower alkoxy or hydroxy-lower alkoxy and provided that $R_2$, $R_3$ and $R_4$ taken independently of each other represent at least one oxygenated substituent; R, $R_2$, $R_3$ and $R_4$ taken as an adjacent pair is methylenedioxy and the optical antipodes thereof.

2. A process for treating proliferative skin diseases which comprises administering to the afflicted human or animal a composition containing 2'-deoxyadenosine in association with a pharmaceutical carrier wherein the concentration of said 2'-deoxyadenosine is effective to alleviate a proliferative skin disease.

* * * * *